United States Patent
Smedley et al.

(10) Patent No.: US 9,220,632 B2
(45) Date of Patent: *Dec. 29, 2015

(54) FLUID INFUSION METHODS FOR OCULAR DISORDER TREATMENT

(71) Applicant: GLAUKOS CORPORATION, Laguna Hills, CA (US)

(72) Inventors: Gregory Smedley, Aliso Viejo, CA (US); David Haffner, Mission Viejo, CA (US); Hosheng Tu, Newport Coast, CA (US)

(73) Assignee: GLAUKOS CORPORATION, Laguna Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/136,753

(22) Filed: Dec. 20, 2013

(65) Prior Publication Data

US 2014/0343475 A1 Nov. 20, 2014

Related U.S. Application Data

(63) Continuation of application No. 11/332,746, filed on Jan. 12, 2006, now Pat. No. 8,617,094, which is a continuation of application No. 10/384,912, filed on Mar. 7, 2003, now Pat. No. 7,186,232.

(60) Provisional application No. 60/362,405, filed on Mar. 7, 2002, provisional application No. 60/363,980, filed on Mar. 14, 2002.

(51) Int. Cl.
*A61F 9/007* (2006.01)
*A61F 9/00* (2006.01)
(Continued)

(52) U.S. Cl.
CPC ........... *A61F 9/00781* (2013.01); *A61F 9/0017* (2013.01); *A61F 9/00745* (2013.01);
(Continued)

(58) Field of Classification Search
CPC .............. A61F 9/00781; A61F 9/0017; A61F 2009/00891; A61F 9/00745; A61M 5/14; A61M 27/002; A61M 2027/004; A61M 2210/0612
See application file for complete search history.

(56) References Cited

U.S. PATENT DOCUMENTS 3,788,327 A 1/1974 Donowitz et al.
3,976,077 A 8/1976 Kerfoot, Jr.
(Continued)

FOREIGN PATENT DOCUMENTS

AU 200072059 7/2001
CA 2244646 8/1998
(Continued)

OTHER PUBLICATIONS

Office Action (Notice of Allowance) in U.S. Appl. No. 10/706,300, filed Nov. 12, 2003, entitled Ocular Implant With Therapeutic Agents and Methods Thereof, Dec. 16, 2009.
(Continued)

*Primary Examiner* — Adam Marcetich
(74) *Attorney, Agent, or Firm* — Knobbe Martens Olson & Bear LLP

(57) ABSTRACT

Methods of treating ocular disorders are disclosed, including: inserting an implant in eye tissue, using an instrument, such that an inlet portion of the implant is in an anterior chamber of an eye and an outlet portion of the implant is in a physiological outflow pathway; removing the instrument from the eye without removing the implant; and conducting fluid comprising a therapeutic substance through the implant and into the physiological outflow pathway. Another method includes inserting an instrument into a physiologic outflow pathway through which aqueous humor drains from an anterior chamber of an eye; separating first and second walls of tissues which comprise the physiologic outflow pathway by injecting a fluid comprising a drug from the instrument while the instrument remains in the physiologic outflow pathway; and withdrawing the instrument with said fluid remaining within the eye such that the drug has a therapeutic effect on the eye.

28 Claims, 6 Drawing Sheets

(51) Int. Cl.
  *A61M 27/00* (2006.01)
  *A61F 9/008* (2006.01)
  *A61M 5/14* (2006.01)

(52) U.S. Cl.
  CPC ......... *A61F2009/00891* (2013.01); *A61M 5/14* (2013.01); *A61M 27/002* (2013.01); *A61M 2210/0612* (2013.01)

(56) References Cited

U.S. PATENT DOCUMENTS

| | | | |
|---|---|---|---|
| 4,037,604 A | 7/1977 | Newkirk | |
| 4,113,088 A | 9/1978 | Binkhorst | |
| 4,168,697 A | 9/1979 | Cantekin | |
| 4,175,563 A | 11/1979 | Arenberg et al. | |
| 4,402,681 A | 9/1983 | Haas et al. | |
| 4,428,746 A | 1/1984 | Mendez | |
| 4,501,274 A | 2/1985 | Skjaerpe | |
| 4,521,210 A | 6/1985 | Wong | |
| 4,554,918 A | 11/1985 | White | |
| 4,583,224 A | 4/1986 | Ishii et al. | |
| 4,604,087 A | 8/1986 | Joseph | |
| 4,632,842 A | 12/1986 | Karwoski et al. | |
| 4,634,418 A | 1/1987 | Binder | |
| 4,642,090 A | 2/1987 | Utrata | |
| 4,713,448 A * | 12/1987 | Balazs et al. | 536/55.1 |
| 4,718,907 A | 1/1988 | Karwoski et al. | |
| 4,722,724 A | 2/1988 | Schocket | |
| 4,733,665 A | 3/1988 | Palmaz | |
| 4,750,901 A | 6/1988 | Molteno | |
| 4,787,885 A | 11/1988 | Binder | |
| 4,804,382 A | 2/1989 | Turina et al. | |
| 4,820,626 A | 4/1989 | Williams et al. | |
| 4,846,172 A * | 7/1989 | Berlin | 606/4 |
| 4,846,793 A | 7/1989 | Leonard et al. | |
| 4,853,224 A | 8/1989 | Wong | |
| 4,863,457 A | 9/1989 | Lee | |
| 4,883,864 A | 11/1989 | Scholz | |
| 4,886,488 A | 12/1989 | White | |
| 4,900,300 A | 2/1990 | Lee | |
| 4,936,825 A | 6/1990 | Ungerleider | |
| 4,946,436 A | 8/1990 | Smith | |
| 4,968,296 A | 11/1990 | Ritch et al. | |
| 4,997,652 A | 3/1991 | Wong | |
| 5,005,577 A | 4/1991 | Frenkel | |
| 5,041,081 A | 8/1991 | Odrich | |
| 5,073,163 A | 12/1991 | Lippman | |
| 5,092,837 A | 3/1992 | Ritch et al. | |
| 5,095,887 A | 3/1992 | Leon et al. | |
| 5,098,443 A | 3/1992 | Parel et al. | |
| 5,127,901 A | 7/1992 | Odrich | |
| 5,129,895 A | 7/1992 | Vassiliadis et al. | |
| 5,164,188 A | 11/1992 | Wong | |
| 5,171,213 A | 12/1992 | Price, Jr. | |
| 5,178,604 A | 1/1993 | Baerveldt et al. | |
| 5,180,362 A | 1/1993 | Worst | |
| 5,207,685 A | 5/1993 | Cinberg et al. | |
| 5,246,451 A | 9/1993 | Trescony et al. | |
| 5,290,295 A | 3/1994 | Querals et al. | |
| 5,300,020 A | 4/1994 | L'Esperance, Jr. | |
| 5,318,513 A | 6/1994 | Leib et al. | |
| 5,334,137 A | 8/1994 | Freeman | |
| 5,338,291 A | 8/1994 | Speckman et al. | |
| 5,346,464 A | 9/1994 | Camras | |
| 5,358,492 A | 10/1994 | Feibus | |
| 5,360,399 A * | 11/1994 | Stegmann | 604/521 |
| 5,370,607 A | 12/1994 | Memmen | |
| 5,370,641 A | 12/1994 | O'Donnell, Jr. | |
| 5,372,577 A | 12/1994 | Ungerleider | |
| 5,397,300 A | 3/1995 | Baerveldt et al. | |
| 5,433,701 A | 7/1995 | Rubinstein | |
| 5,443,505 A | 8/1995 | Wong et al. | |
| 5,454,796 A | 10/1995 | Krupin | |
| 5,472,440 A | 12/1995 | Beckman | |
| 5,476,445 A | 12/1995 | Baerveldt et al. | |
| 5,486,165 A | 1/1996 | Stegmann | |
| 5,516,522 A | 5/1996 | Peyman et al. | |
| 5,520,631 A | 5/1996 | Nordquist et al. | |
| 5,557,453 A | 9/1996 | Schalz et al. | |
| 5,558,629 A | 9/1996 | Baerveldt et al. | |
| 5,558,630 A | 9/1996 | Fisher | |
| 5,558,637 A | 9/1996 | Allonen et al. | |
| 5,562,641 A | 10/1996 | Flomenblit et al. | |
| RE35,390 E | 12/1996 | Smith | |
| 5,599,534 A | 2/1997 | Himmelstein et al. | |
| 5,601,094 A | 2/1997 | Reiss | |
| 5,601,549 A | 2/1997 | Miyagi | |
| 5,626,558 A | 5/1997 | Suson | |
| 5,626,559 A | 5/1997 | Solomon | |
| 5,629,008 A | 5/1997 | Lee | |
| 5,639,278 A | 6/1997 | Dereume et al. | |
| 5,651,783 A | 7/1997 | Reynard | |
| 5,652,014 A | 7/1997 | Galin et al. | |
| 5,665,114 A | 9/1997 | Weadock et al. | |
| 5,670,161 A | 9/1997 | Healy et al. | |
| 5,676,679 A | 10/1997 | Simon et al. | |
| 5,681,275 A | 10/1997 | Ahmed | |
| 5,681,323 A | 10/1997 | Arick | |
| 5,702,414 A | 12/1997 | Richter et al. | |
| 5,702,419 A | 12/1997 | Berry et al. | |
| 5,704,907 A | 1/1998 | Nordquist et al. | |
| 5,713,844 A | 2/1998 | Peyman | |
| 5,723,005 A | 3/1998 | Herrick | |
| 5,741,333 A | 4/1998 | Frid | |
| 5,743,868 A | 4/1998 | Brown et al. | |
| 5,752,928 A | 5/1998 | De Roulhac et al. | |
| 5,766,242 A | 6/1998 | Wong et al. | |
| 5,766,243 A | 6/1998 | Christensen et al. | |
| 5,767,079 A | 6/1998 | Glaser et al. | |
| 5,785,674 A | 7/1998 | Mateen | |
| 5,800,376 A | 9/1998 | Vaskelis et al. | |
| 5,807,302 A | 9/1998 | Wandel | |
| 5,810,870 A | 9/1998 | Myers et al. | |
| 5,824,072 A | 10/1998 | Wong | |
| 5,830,139 A | 11/1998 | Abreu | |
| 5,830,171 A | 11/1998 | Wallace | |
| 5,833,694 A | 11/1998 | Poncet | |
| 5,836,939 A | 11/1998 | Negus et al. | |
| 5,840,041 A | 11/1998 | Petter et al. | |
| 5,865,831 A | 2/1999 | Cozean et al. | |
| 5,868,697 A | 2/1999 | Richter et al. | |
| 5,879,319 A | 3/1999 | Pynson et al. | |
| 5,882,327 A | 3/1999 | Jacob | |
| 5,886,822 A | 3/1999 | Spitzer | |
| 5,891,084 A | 4/1999 | Lee | |
| 5,893,837 A | 4/1999 | Eagles et al. | |
| 5,908,449 A | 6/1999 | Bruchman et al. | |
| 5,932,299 A | 8/1999 | Katoot | |
| 5,968,058 A | 10/1999 | Richter et al. | |
| 5,980,928 A | 11/1999 | Terry | |
| 5,981,598 A | 11/1999 | Tatton | |
| 6,004,302 A | 12/1999 | Brierley | |
| 6,007,510 A | 12/1999 | Nigam | |
| 6,007,511 A * | 12/1999 | Prywes | 604/9 |
| 6,033,418 A | 3/2000 | Gordon et al. | |
| 6,033,434 A | 3/2000 | Borghi | |
| 6,045,557 A | 4/2000 | White et al. | |
| 6,050,970 A | 4/2000 | Baerveldt | |
| 6,050,999 A | 4/2000 | Paraschac et al. | |
| 6,059,772 A | 5/2000 | Hsia et al. | |
| 6,059,812 A | 5/2000 | Clerc et al. | |
| 6,063,116 A | 5/2000 | Kelleher | |
| 6,063,396 A | 5/2000 | Kelleher | |
| 6,071,286 A | 6/2000 | Mawad | |
| 6,077,299 A | 6/2000 | Adelberg et al. | |
| 6,102,045 A | 8/2000 | Nordquist et al. | |
| 6,123,668 A | 9/2000 | Abreu | |
| 6,142,990 A | 11/2000 | Burk | |
| 6,165,210 A | 12/2000 | Lau et al. | |
| 6,168,575 B1 | 1/2001 | Soltanpour | |
| 6,174,305 B1 | 1/2001 | Mikus et al. | |
| 6,187,016 B1 | 2/2001 | Hedges et al. | |
| 6,193,656 B1 | 2/2001 | Jeffries et al. | |
| 6,197,056 B1 | 3/2001 | Schachar | |

(56) References Cited

U.S. PATENT DOCUMENTS

| | | | |
|---|---|---|---|
| 6,203,513 B1 | 3/2001 | Yaron et al. | |
| 6,217,895 B1 | 4/2001 | Guo et al. | |
| 6,221,078 B1 | 4/2001 | Bylsma | |
| 6,228,873 B1 | 5/2001 | Brandt et al. | |
| 6,231,597 B1 | 5/2001 | Deem et al. | |
| 6,241,721 B1 * | 6/2001 | Cozean et al. | 606/6 |
| 6,251,090 B1 | 6/2001 | Avery et al. | |
| 6,254,612 B1 | 7/2001 | Hieshima | |
| 6,261,256 B1 | 7/2001 | Ahmed | |
| 6,266,182 B1 | 7/2001 | Morita | |
| 6,268,398 B1 | 7/2001 | Ghosh et al. | |
| 6,287,256 B1 | 9/2001 | Park et al. | |
| 6,287,313 B1 | 9/2001 | Sasso | |
| 6,299,603 B1 | 10/2001 | Hecker et al. | |
| 6,299,895 B1 | 10/2001 | Hammang et al. | |
| 6,306,120 B1 | 10/2001 | Tan | |
| 6,331,313 B1 | 12/2001 | Wong et al. | |
| 6,342,058 B1 | 1/2002 | Portney | |
| 6,348,042 B1 | 2/2002 | Warren, Jr. | |
| 6,375,642 B1 * | 4/2002 | Grieshaber et al. | 604/294 |
| 6,378,526 B1 | 4/2002 | Bowman et al. | |
| 6,413,540 B1 | 7/2002 | Yaacobi | |
| 6,416,777 B1 | 7/2002 | Yaacobi | |
| 6,428,501 B1 | 8/2002 | Reynard | |
| 6,436,427 B1 | 8/2002 | Hammang et al. | |
| 6,450,937 B1 | 9/2002 | Mercereau et al. | |
| 6,450,984 B1 | 9/2002 | Lynch et al. | |
| 6,464,724 B1 | 10/2002 | Lynch et al. | |
| 6,471,666 B1 | 10/2002 | Odrich | |
| 6,524,275 B1 | 2/2003 | Lynch et al. | |
| 6,530,896 B1 | 3/2003 | Elliott | |
| 6,533,768 B1 | 3/2003 | Hill | |
| 6,533,769 B2 | 3/2003 | Holmen | |
| 6,544,249 B1 | 4/2003 | Yu et al. | |
| 6,548,078 B2 | 4/2003 | Guo et al. | |
| 6,579,235 B1 | 6/2003 | Abita et al. | |
| 6,585,680 B2 | 7/2003 | Bugge | |
| 6,595,945 B2 | 7/2003 | Brown | |
| 6,596,296 B1 | 7/2003 | Nelson et al. | |
| 6,622,473 B2 | 9/2003 | Lynch et al. | |
| 6,626,858 B2 | 9/2003 | Lynch et al. | |
| 6,629,981 B2 | 10/2003 | Bui et al. | |
| 6,638,239 B1 | 10/2003 | Bergheim et al. | |
| 6,666,841 B2 | 12/2003 | Gharib et al. | |
| 6,699,211 B2 | 3/2004 | Savage | |
| 6,726,664 B2 | 4/2004 | Yaron et al. | |
| D490,152 S | 5/2004 | Myall et al. | |
| 6,736,791 B1 | 5/2004 | Tu et al. | |
| 6,780,165 B2 | 8/2004 | Kadziauskas et al. | |
| 6,783,544 B2 | 8/2004 | Lynch et al. | |
| 6,827,699 B2 | 12/2004 | Lynch et al. | |
| 6,827,700 B2 | 12/2004 | Lynch et al. | |
| 6,955,656 B2 | 10/2005 | Bergheim et al. | |
| 7,033,603 B2 | 4/2006 | Nelson et al. | |
| 7,060,094 B2 | 6/2006 | Shahinpoor et al. | |
| 7,094,225 B2 | 8/2006 | Tu et al. | |
| 7,135,009 B2 | 11/2006 | Tu et al. | |
| 7,186,232 B1 * | 3/2007 | Smedley et al. | 604/8 |
| 2002/0013546 A1 | 1/2002 | Grieshaber et al. | |
| 2002/0013572 A1 | 1/2002 | Berlin | |
| 2002/0026200 A1 | 2/2002 | Savage | |
| 2002/0072673 A1 | 6/2002 | Yamamoto et al. | |
| 2002/0099434 A1 | 7/2002 | Buscemi et al. | |
| 2002/0111608 A1 * | 8/2002 | Baerveldt et al. | 606/6 |
| 2002/0128704 A1 | 9/2002 | Daum et al. | |
| 2002/0133168 A1 | 9/2002 | Smedley et al. | |
| 2002/0143284 A1 | 10/2002 | Tu et al. | |
| 2002/0165478 A1 | 11/2002 | Gharib et al. | |
| 2002/0165522 A1 | 11/2002 | Holmen | |
| 2002/0169130 A1 | 11/2002 | Tu et al. | |
| 2002/0188308 A1 * | 12/2002 | Tu et al. | 606/167 |
| 2003/0014021 A1 | 1/2003 | Holmen | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0088260 A1 | 5/2003 | Smedley et al. | |
| 2003/0097117 A1 | 5/2003 | Buono | |
| 2003/0097151 A1 | 5/2003 | Smedley et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0229303 A1 | 12/2003 | Haffner et al. | |
| 2003/0236483 A1 | 12/2003 | Ren | |
| 2003/0236484 A1 | 12/2003 | Lynch et al. | |
| 2004/0024345 A1 | 2/2004 | Gharib et al. | |
| 2004/0050392 A1 | 3/2004 | Tu et al. | |
| 2004/0092548 A1 | 5/2004 | Embleton et al. | |
| 2004/0102729 A1 | 5/2004 | Haffner et al. | |
| 2004/0111050 A1 | 6/2004 | Smedley et al. | |
| 2004/0127843 A1 | 7/2004 | Tu et al. | |
| 2004/0254520 A1 | 12/2004 | Porteous et al. | |
| 2005/0038334 A1 | 2/2005 | Lynch et al. | |
| 2005/0049578 A1 | 3/2005 | Tu et al. | |
| 2005/0119737 A1 | 6/2005 | Bene et al. | |
| 2005/0192527 A1 | 9/2005 | Gharib et al. | |

FOREIGN PATENT DOCUMENTS

| | | |
|---|---|---|
| DE | 198 40 047 | 3/2000 |
| EP | 0 858 788 | 8/1998 |
| EP | 0 898 947 | 3/1999 |
| EP | 1 114 627 | 11/2001 |
| FR | 2710269 | 3/1995 |
| FR | 2 721 499 | 12/1995 |
| FR | 2757068 A1 | 6/1998 |
| GB | 2 296 663 | 7/1996 |
| JP | 11-123205 | 5/1999 |
| WO | WO 89/00869 | 2/1989 |
| WO | WO 91/18568 | 12/1991 |
| WO | WO 92/19294 | 11/1992 |
| WO | WO 94/13234 | 6/1994 |
| WO | WO 94/21205 | 9/1994 |
| WO | WO 95/08310 | 3/1995 |
| WO | WO 98/30181 | 7/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | WO 00/64389 | 11/2000 |
| WO | WO 00/64390 | 11/2000 |
| WO | WO 00/64391 | 11/2000 |
| WO | WO 00/64393 | 11/2000 |
| WO | WO 00/72788 | 12/2000 |
| WO | WO 01/50943 | 7/2001 |
| WO | WO 01/78631 | 10/2001 |
| WO | WO 01/78656 | 10/2001 |
| WO | WO 03/015659 | 2/2003 |
| WO | WO 03/073968 | 9/2003 |

OTHER PUBLICATIONS

Office Action (Final) in U.S. Appl. No. 10/889,254, filed Jul. 12, 2004, entitled Ocular Implant With Anchor and Therapeutic Agent, Jan. 6, 2010.

Office Action (Interview Summary) in U.S. Appl. No. 10/889,254, filed Jul. 12, 2004, entitled Ocular Implant With Anchor and Therapeutic Agent, Mar. 3, 2010.

Office Action in U.S. Appl. No. 10/889,254, filed Jul. 12, 2004, entitled Ocular Implant With Anchor and Therapeutic Agent, Jun. 18, 2010.

Office Action (Final) in U.S. Appl. No. 10/889,254, filed Jul. 12, 2004, entitled Ocular Implant With Anchor and Therapeutic Agent, Jan. 21, 2011.

Office Action (Restriction Requirement) in U.S. Appl. No. 10/889,254, filed Jul. 12, 2004, entitled Ocular Implant With Anchor and Therapeutic Agent.

Office Action in U.S. Appl. No. 10/889,254, filed Jul. 12, 2004, entitled Ocular Implant With Anchor and Therapeutic Agent, Jan. 17, 2007.

Office Action (Final) in U.S. Appl. No. 10/889,254, filed Jul. 12, 2004, entitled Ocular Implant With Anchor and Therapeutic Agent, Aug. 6, 2007.

(56) References Cited

OTHER PUBLICATIONS

Office Action in U.S. Appl. No. 10/889,254, filed Jul. 12, 2004, entitled Ocular Implant With Anchor and Therapeutic Agent, Nov. 23, 2007.
Office Action (Interview Summary) in U.S. Appl. No. 10/889,254, filed Jul. 12, 2004, entitled Ocular Implant With Anchor and Therapeutic Agent, Jun. 2, 2008.
Office Action (Final) in U.S. Appl. No. 10/889,254, filed Jul. 12, 2004, entitled Ocular Implant With Anchor and Therapeutic Agent, Aug. 18, 2008.
Office Action in U.S. Appl. No. 10/889,254, filed Jul. 12, 2004, entitled Ocular Implant With Anchor and Therapeutic Agent, Apr. 13, 2009.
Office Action (Notice to Provide an Applicant's Record Under 37 CFR 1.251 to Support the Reconstruction of the Application) in U.S. Appl. No. No. 10/706,300, filed Nov. 12, 2003, entitled Ocular Implant With Therapeutic Agents and Methods Thereof, Dec. 17, 2004.
Office Action (Restriction Requirement) in U.S. Appl. No. 10/706,300, filed Nov. 12, 2003, entitled Ocular Implant With Therapeutic Agents and Methods Thereof, Jun. 12, 2006.
Office Action (Final) in U.S. Appl. No. 10/706,300, filed Nov. 12, 2003, entitled Ocular Implant With Therapeutic Agents and Methods Thereof, Feb. 21, 2007.
Office Action in U.S. Appl. No. 10/706,300, filed Nov. 12, 2003, entitled Ocular Implant With Therapeutic Agents and Methods Thereof, Aug. 24, 2007.
Office Action (Notice of Non-Complidnt Amendment) in U.S. Appl. No. 10/706,300, filed Nov. 12, 2003, entitled Ocular Implant With Therapeutic Agents and Methods Thereof, Apr. 1, 2008.
Office Action (Interview Summary) in U.S. Appl. No. 10/706,300, filed Nov. 12, 2003, entitled Ocular Implant With Therapeutic Agents and Methods Thereof, May 21, 2008.
Office Action (Final) in U.S. Appl. No. 10/706,300, filed Nov. 12, 2003, entitled Ocular Implant With Therapeutic Agents and Methods Thereof, Jul. 29, 2008.
Office Action (Interview Summary) in U.S. Appl. No. 10/706,300, filed Nov. 12, 2003, entitled Ocular Implant With Therapeutic Agents and Methods Thereof, Dec. 11, 2008.
Office Action in U.S. Appl. No. 10/706,300, filed Nov. 12, 2003, entitled Ocular Implant With Therapeutic Agents and Methods thereof, Mar. 17, 2009.
Office Action (Interview Summary) in U.S. Appl. No. 10/706,300, filed Nov. 12, 2003, entitled Ocular Implant With Therapeutic Agents and Methods Thereof, Jun. 9, 2009.
International Search Report for PCT/US 00/15200 mailed Oct. 5, 2000 European Patent Office.
Anselm Kampik and Franz Grehn, *Nutzen und Risiken augenärztlicher Therapie, Hauptreferate der XXXIII. Essener Fortbildung für Augenärzte*, Dec. 1998. (English translated version enclosed Benefits and Risks of Ophthalmological Therapy.)
Phillip C. Jacobi, MD, Thomas S. Dietlein, MD, and Gunter K. Krieglstein, MD., *Goniocurettage for Removing Trabecular Meshwork: Clinical Results of a New Surgical Technique in Advanced Cronic Open-Angle Glaucoma*, American Journal of Ophthalmology, May 1999, pp. 505-510.
Philip C. Jacobi, MD, Thomas S. Dietlein, MD, and Gunter K. Krieglstein, MD., *Bimanual Trabecular Aspiration in Pseudoexfoliation Glaucoma, Ophthalmology*, 1998, vol. 105, No. 5, May 1998, pp. 886-894.
Phillip C. Jacobi, MD, Thomas S. Dietlein, MD, and Gunter K. Krieglstein, MD., *Microendoscopic Trabecular Surgery in Glaucoma Management*, Ophthalmology, 1999, vol. 106, No. 3, pp. 538-544.
Arthur L. Schwartz, MD, and Douglas R. Anderson, MD, *Trabecular Surgery*, Arch Ophthalmol, vol. 92, Aug. 1974, pp. 134-138.
R.A. Hill, Q. Ren, D.D. Nguyen, L-H Liaw, and M.W. Berns, *Free-Electron Laser (FEL) Ablation of Ocular Tissues*, Lasesr Med Sci 1998, pp. 13:219-226.

Maurice H. Luntz, MD, and D.G. Livingston, B.SC., *Trabeculotomy AB Externo and Trabeculectomy in Congenital and Adult-Onset Glaucoma*, American Journal of Ophthalmology, Feb. 1977, vol. 83, No. 2, pp. 174-179.
W.M. Grant, MD, *Further Studies on Facility of Flow Through the Trabecular Meshwork*, A.M.A. Archives of Ophthalmololgy, Oct. 1958, vol. 60, pp. 523-533.
Richard A. Hill, MD, George Baerveldt, MD, Serdar A. Ozler, MD, Michael Pickford, BA, Glen A. Profeta, BS, and Michael W. Berns,PhD, *Laser Trabecular Ablation (LTA)*, Laser in Surgery and Medicine, 1991, vol. 11, pp. 341-346.
Detlev Spiegel, MD, Karin Kobuch, MD, Richard A. Hill, MD, Ronald L. Gross, MD, *Schlemm's Canal Implant: A New Method to Lower Intraocular Pressure in Patients With POAG*, Ophthalmic Surgery and Lasers, Jun. 1999, vol. 30, No. 6, pp. 492-494.
Hans Hoerauf, Christopher Wirbelauer, Christian Scholz, Ralf Engelhardt, Peter Koch, Horst Laqua, and Reginald Birngruber, *Slit-Lamp-Adapted Optical Coherence Tomography of the Anteriuor Segment*, Graefe's Arch Clin. Exp. Ophthalmol, May 1999, vol. 238, pp. 8-18.
Sumita Radhakrishnan, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.
I. Grierson, R.C. Howes, and Q. Wang, *Age-related Changes in the Canal of Schlemm*, Exp. Eye Res., 1984, vol. 39, pp. 505-512.
Luanna K. Putney, Cecile Rose T. Vibat, and Martha E. O'Donnell, *Intracellular Cl Regulates Na-K-Cl Cotransport Activity in Human Trabecular Meshwork Cells*, 1999 American Physiological Society, Sep. 1999, pp. C373 through C383.
William Tatton, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.
Robert W. Nickells, *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S-161.
Yasuhiro Matsumoto and Douglas H. Johnson, *Trabecular Meshwork Phagocytosis in Graucomatous Eyes*, Ophthalmologica 1977, vol. 211, pp. 147-152.
M. Bruce Shields, MD, *A Study Guide for Glaucoma: Aqueous Humor Dynamics*, Copyright 1982, pp. 6-43.
W.G. Tatton, *Apoptotic Mechanisms in Neurodegeneration: Possible Relevance to Glaucoma*, European Journal of Ophthalmology, Jan.-Mar. 1999, vol. 9, Supplement 1, pp. S22 through S29.
L. Jay Katz, M.D., *A Call for Innovative Operations for Glaucoma*, Arch Ophthalmology, Mar. 2000, vol. 118, pp. 412-413.
Cindy K. Bahler, BS, Gegrory T. Smedley, PhD, Jianbo Zhou, PhD, Douglas H. Johnson, MD., *American Journal of Ophthalmology*, Dec. 2004, vol. 138.
Jianbo Zhou, PhD, Gregory T. Smedley, PhD., *A Trabecular Bypass Flow Hypothesis*, Feb. 2005, vol. 14 No. 1.
U.S. Appl. No. 09/452,963, filed Dec. 2, 1999. Title: *Expandable/Retractable Stent for Venous and Valvular Annulus Use*.
Vincente, L. Jocson, M.D.; *Air Trabeculotomy*; American Journal of Ophthalmolgy: vol. 79, No. 1, Jan.-Jun. 1975; pp. 107-111.
Daniel A. Fletcher, Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.
Hyaluronan, "Medical Applications", Encyclopedia Article from http://en.wikipedia.org/wiki/Hyaluronic_acid, accessed Sep. 27, 2010 (2 pages).
Kim et al., Controlled Drug Release from an Ocular Implant: An Evaluation Using Dynamic Three-Diminsional Magnetic Resonance Imaging. Invest Ophthalmol Vis Sci. 2004;45:2722-2731 (10 pages).
Olsen, et al., "Cannulation of the Suprachoroidal Space: A Novel Drug Delivery Methodology to the Posterior Segment", American Journal of Ophthalmology, Nov. 2006, pp. 777-787.e2 (13 pages).

(56) References Cited

OTHER PUBLICATIONS

Rosenberg, et al., "Implants in Glaucoma Surgery", The Glaucomas, 1996, Chapter 88, pp. 1783-1807 (27 pages).

Manuel Uribe Troncoso, M.D., *Cyclodialysis with Insertion of a Metal Implant in the Treatment of Glaucoma*, Read before the Section on Ophthalmology at the Ninetieth Annual Session of the American Medical Association, St. Louis, May 17, 1939, Archives of Ophthalmology, pp. 270-300, downloaded from www.archophthalmol.com on Aug. 5, 2010 (31 pages).

Troncoso, Manuel U., Tantalum implants for inducing hypotony, American Journal of Ophthalmology, vol. 32, No. 4, Apr. 1949, pp. 499-508 (11 pages).

* cited by examiner

FLUID INFUSION METHODS FOR OCULAR DISORDER TREATMENT

CROSS REFERENCE TO RELATED APPLICATION

This application is a continuation application of U.S. patent application Ser. No. 11/332,746, entitled, "Fluid Infusion Methods for Ocular Disorder Treatment," filed Jan. 12, 2006, which is a continuation application of U.S. patent application Ser. No. 10/384,912, entitled "Fluid Infusion Methods for Glaucoma Treatment," filed Mar. 7, 2003, now U.S. Pat. No. 7,186,232 B1, issued Mar. 6, 2007, which application claims the priority benefit of U.S. Provisional Application No. 60/362,405, entitled "Apparatus and Combination Therapy for Treating Glaucoma," filed Mar. 7, 2002, and U.S. Provisional Application No. 60/363,980, entitled "Means and Procedures for Implanting a Glaucoma Shunt," filed Mar. 14, 2002, the entireties of which are hereby incorporated by reference.

BACKGROUND OF THE INVENTION

1. Field of the Invention

This invention relates to reducing intraocular pressure within the animal eye. More particularly, this invention relates to a treatment of glaucoma wherein aqueous humor is permitted to flow out of an anterior chamber of the eye through a surgically implanted pathway. Furthermore, this invention relates to directly dilating Schlemm's canal and/or aqueous collector channels by injecting fluid through the implanted pathway of a stent.

2. Description of the Related Art

A human eye is a specialized sensory organ capable of light reception and is able to receive visual images. Aqueous humor is a transparent liquid that fills the region between the cornea, at the front of the eye, and the lens. A trabecular meshwork, located in an anterior chamber angle formed between the iris and the cornea, serves as a drainage channel for aqueous humor from the anterior chamber, which maintains a balanced pressure within the anterior chamber of the eye.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor (hereinafter referred to as "aqueous") to enter Schlemm's canal, which then empties into aqueous collector channels in the posterior wall of Schlemm's canal and then into aqueous veins, which form the episcleral venous system. Aqueous is continuously secreted by a ciliary body around the lens, so there is a constant flow of aqueous from the ciliary body to the anterior chamber of the eye. Pressure within the eye is determined by a balance between the production of aqueous and its exit through the trabecular meshwork (major route) and uveo-scleral outflow (minor route). The portion of the trabecular meshwork adjacent to Schlemm's canal (the juxtacanilicular meshwork) causes most of the resistance to aqueous outflow.

Glaucoma is broadly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye. Open-angle glaucoma is any glaucoma in which the exit of aqueous through the trabecular meshwork is diminished while the angle of the anterior chamber remains open. For most cases of open-angle glaucoma, the exact cause of diminished filtration is unknown. Primary open-angle glaucoma is the most common of the glaucomas, and is often asymptomatic in the early to moderately advanced stages of glaucoma. Patients may suffer substantial, irreversible vision loss prior to diagnosis and treatment. However, there are secondary open-angle glaucomas that may include edema or swelling of the trabecular spaces (e.g., from corticosteroid use), abnormal pigment dispersion, or diseases such as hyperthyroidism that produce vascular congestion.

All current therapies for glaucoma are directed toward decreasing intraocular pressure. Currently recognized categories of drug therapy for glaucoma include: (1) Miotics (e.g., pilocarpine, carbachol, and acetylcholinesterase inhibitors), (2) Sympathomimetics (e.g., epinephrine and dipivalyl-epinephxine), (3) Beta-blockers (e.g., betaxolol, levobunolol and timolol), (4) Carbonic anhydrase inhibitors (e.g., acetazolamide, methazolamide and ethoxzolamide), and (5) Prostaglandins (e.g., metabolite derivatives of arachindonic acid). Medical therapy includes topical ophthalmic drops or oral medications that reduce the production of aqueous or increase the outflow of aqueous. However, drug therapies for glaucoma are sometimes associated with significant side effects. The most frequent and perhaps most serious drawback to drug therapy is that patients, especially the elderly, often fail to correctly self-medicate. Such patients forget to take their medication at the appropriate times or else administer eye drops improperly, resulting in under- or overdosing. Because the effects of glaucoma are irreversible, when patients dose improperly, allowing ocular concentrations to drop below appropriate therapeutic levels, further permanent damage to vision occurs. Furthermore, current drug therapies are targeted to be deposited directly into the ciliary body where the aqueous is produced. And, current therapies do not provide for a continuous slow-release of the drug. When drug therapy fails, surgical therapy is pursued.

Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if ocular morbidity associated with trabeculectomy could be decreased. The current morbidity associated with trabeculectomy consists of failure (10-15%); infection (a life long risk of 2-5%); choroidal hemorrhage, a severe internal hemorrhage from low intraocular pressure, resulting in visual loss (1%); cataract formation; and hypotony maculopathy (potentially reversible visual loss from low intraocular pressure). For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Q-switched Neodynium (Nd) YAG lasers also have been investigated as an optically invasive trabeculopuncture technique for creating full-thickness holes in trabecular meshwork. However, the relatively small hole created by this trabeculopuncture technique exhibits a filling-in effect and fails.

Goniophotoablation is disclosed by Berlin in U.S. Pat. No. 4,846,172 and involves the use of an excimer laser to treat glaucoma by ablating the trabecular meshwork. This method did not succeed in a clinical trial. Hill et al. used an Erbium YAG laser to create full-thickness holes through trabecular meshwork (Hill et al., Lasers in Surgery and Medicine 11:341346, 1991). This laser trabecular ablation technique was investigated in a primate model and a limited human clinical trial at the University of California, Irvine. Although ocular morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage is an "ab interno" (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanalostomy (VC) and non-penetrating trabeculectomy (NPT) are two new variations of filtering surgery. These are "ab externo" (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous through the surgical opening will continue. The risk of placing a glaucoma drainage device also includes hemorrhage, infection, and diplopia (double vision).

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and involve a prolonged recovery time for vision. The complications of existing filtration surgery have prompted ophthalmic surgeons to find other approaches to lowering intraocular pressure.

Because the trabecular meshwork and juxtacanilicular tissue together provide the majority of resistance to the outflow of aqueous, they are logical targets for surgical removal in the treatment of open-angle glaucoma. In addition, minimal amounts of tissue need be altered and existing physiologic outflow pathways can be utilized.

As reported in Arch. Ophthalm. (2000) 118:412, glaucoma remains a leading cause of blindness, and filtration surgery remains an effective, important option in controlling glaucoma. However, modifying existing filtering surgery techniques in any profound way to increase their effectiveness appears to have reached a dead end. The article further states that the time has come to search for new surgical approaches that may provide better and safer care for patients with glaucoma.

What is needed, therefore, is an extended, site-specific treatment method for placing a hollow trabecular microstent ab interno for diverting aqueous humor in an eye from the anterior chamber into Schlemm's canal. In some aspect of the present invention, it is provided a method for injecting fluid through the common hollow lumen of the microstent to therapeutically dilate Schlemm's canal and the aqueous collector channels.

SUMMARY OF THE INVENTION

A device and methods are provided for improved treatment of intraocular pressure due to glaucoma. A hollow trabecular microstent is adapted for implantation within a trabecular meshwork of an eye such that aqueous humor flows controllably from an anterior chamber of the eye to Schlemm's canal, bypassing the trabecular meshwork. The trabecular microstent comprises a quantity of pharmaceuticals effective in treating glaucoma, which are controllably released from the device into cells of the trabecular meshwork and/or Schlemm's canal. Depending upon the specific treatment contemplated, pharmaceuticals may be utilized in conjunction with the trabecular microstent such that aqueous flow either increases or decreases as desired. Placement of the trabecular microstent within the eye and incorporation, and eventual release, of a proven pharmaceutical glaucoma therapy will reduce, inhibit or slow the effects of glaucoma.

One aspect of the invention provides an axisymmetric trabecular microstent that is implantable within an eye. The microstent comprises an inlet section containing at least one lumen and one inlet opening, an outlet section having at least one lumen that connects to at least one outlet opening. In some aspect of the present invention, the microstent further comprises a flow-restricting member within the lumen that is configured to partially prevent back flow from passing through the flow-restricting member. The microstent further comprises a middle section that is fixedly attached to the outlet section having at least one lumen in fluid communication with the lumen of the outlet section. The middle section is fixedly attached to the inlet section and the lumen within the middle section is in fluid communication with the lumen of the inlet section. The device is configured to permit fluid entering the lumen of the inlet section to pass through the flow-restricting member, enter the lumen of the middle section, pass into the lumen of the outlet section, and then exit the outlet section.

Another aspect of the invention provides a method of treating glaucoma. The method comprises providing fluid through the lumen of the microstent to therapeutically dilate the aqueous cavity. The term "aqueous cavity" herein refers to any one or more of the downstream aqueous passageways "behind" the trabecular meshwork, including, without limitation, Schlemm's canal, the aqueous collector channels, and episcleral veins. In one embodiment, the fluid contains therapeutic substance, including pharmaceuticals, genes, growth factors, enzymes and like. In another embodiment, the fluid contains sterile saline, viscoelastic, or the like. The mode of fluid injection may be a pulsed mode, an intermittent mode or a programmed mode. In one aspect, the pressure of the fluid therapy is effective to cause therapeutic effects on the tissue of the aqueous cavity. In another aspect, the fluid pressure is effective to cause the dilation of the aqueous cavity beyond the tissue elastic yield point for permanent (i.e., plastic) deformation. In other embodiment, the fluid is at an elevated pressure effective to cause plastic deformation for at least a portion of the aqueous cavity.

Another aspect of the invention provides an apparatus for implanting a trabecular microstent within an eye and dilating the aqueous cavity. The apparatus comprises a syringe portion and a cannula portion that has proximal and distal ends. The proximal end of the cannula portion is attached to the syringe portion. The cannula portion further comprises a first lumen and at least one irrigating hole disposed between the proximal and distal ends of the cannula portion. The irrigating hole is in fluid communication with the lumen. The apparatus further includes a holder including a second lumen for holding the trabecular microstent. A distal end of the second lumen opens to the distal end of the cannula portion, and a proximal end of the second lumen is separated from the first lumen of the cannula portion. The holder holds the trabecular microstent during implantation of the device within the eye, and the holder releases the trabecular microstent when a practitioner activates deployment of the device.

Another aspect of the invention provides a method of implanting a trabecular microstent within an eye. The method comprises creating a first incision in a cornea on a first side of the eye, wherein the first incision passes through the cornea into an anterior chamber of the eye. The method further comprises passing an incising device through the first incision and moving a distal end of the incising device across the anterior chamber to a trabecular meshwork residing on a second side of the eye, and using the incising device to create a second incision. The second incision is in the trabecular meshwork, passing from the anterior chamber through the trabecular meshwork into a Schlemm's canal. The method further comprises inserting the trabecular microstent into a distal space of a delivery applicator. The delivery applicator comprises a cannula portion having a distal end and a proximal end attached to a syringe portion. The cannula portion has at least one lumen and at least one irrigating hole disposed between proximal and distal ends of the cannula portion. The irrigating hole is in fluid communication with the lumen. The distal space comprises a holder that holds the trabecular microstent during delivery and releases the trabecular microstent when a practitioner activates deployment of the device. The method further comprises advancing the cannula portion and the trabecular microstent through the first incision, across the anterior chamber and into the second incision, wherein an outlet section of the trabecular microstent is implanted into Schlemm's canal while an inlet section of the trabecular microstent remains in fluid communication with the anterior chamber. The method still further comprises releasing the trabecular microstent from the holder of the delivery applicator.

One aspect of the invention includes a method of treating glaucoma, including inserting a stent through an incision in an eye; the stent having an inflow portion that is in fluid communication with an outflow portion of the stent; transporting the stent from the incision through the anterior chamber of the eye to an aqueous cavity of the eye, such that the inflow portion of the stent is positioned in the anterior chamber and the outflow portion of the stent is positioned at the aqueous cavity; and infusing fluid from the inflow portion to the outflow portion of the stent.

Some embodiments further include closing the incision, leaving the stent in the eye such that the inflow portion of the stent is positioned in the anterior chamber of the eye and the outflow portion of the stent is positioned in Schlemm's canal.

Some embodiments further include positioning the stent such that fluid communicating from the inflow portion to the outflow portion of the stent bypasses the trabecular meshwork of the eye.

In some embodiments fluid is infused through a lumen of the stent. In some embodiments the aqueous cavity is Schlemm's canal. In other embodiments the aqueous cavity is an aqueous collector channel.

In some embodiments, the infusing further comprises injecting the fluid in at least one of a pulsed mode, an intermittent mode, and a programmed mode.

In some embodiments the infusing of fluid is at a pressure sufficient to cause plastic deformation of at least a portion of the aqueous cavity.

In a preferred arrangement, the fluid is at least one of a salt solution or viscoelastic.

In some arrangements the infusing further comprises coupling the inflow portion of the stent with a fluid delivery element that transmits the fluid to the stent. In an embodiment the coupling comprises securing a screw thread arrangement of the fluid delivery element with a receiving thread arrangement of the stent.

In certain preferred arrangements, the fluid comprises a therapeutic substance such as a pharmaceutical, a gene, a growth factor, and/or an enzyme.

In other preferred arrangements, the fluid comprises the fluid comprises a therapeutic substance such as an antiglaucoma drug, a beta-adrenergic antagonist, a TGF-beta compound, and/or an antibiotic.

Some embodiments provide that a temperature of the fluid is raised sufficiently to enhance the plastic deformation. And some embodiments provide that a pH of the fluid is adjusted sufficiently to enhance the plastic deformation.

In some arrangements the method further includes vibrating a tissue of the eye.

One aspect of the invention includes a method of treating glaucoma, including inserting a stent through an incision in an eye; the stent having an inflow portion that is in fluid communication with an outflow portion of the stent; positioning the stent such that the inflow portion of the stent is positioned in the anterior chamber of the eye and the outflow portion of the stent is positioned at an aqueous cavity; and infusing fluid from the inflow portion to the outflow portion of the stent.

In some arrangements the aqueous cavity is Schlemm's canal. In certain arrangements, the method further comprises positioning the stent such that the outflow portion of the stent is in Schlemm's canal. In some arrangements the aqueous cavity is an aqueous collector channel.

DETAILED DESCRIPTION OF THE PREFERRED EMBODIMENTS

The preferred embodiments of the present invention described below relate particularly to surgical and therapeutic treatment of glaucoma through reduction of intraocular pressure. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Figure 1:
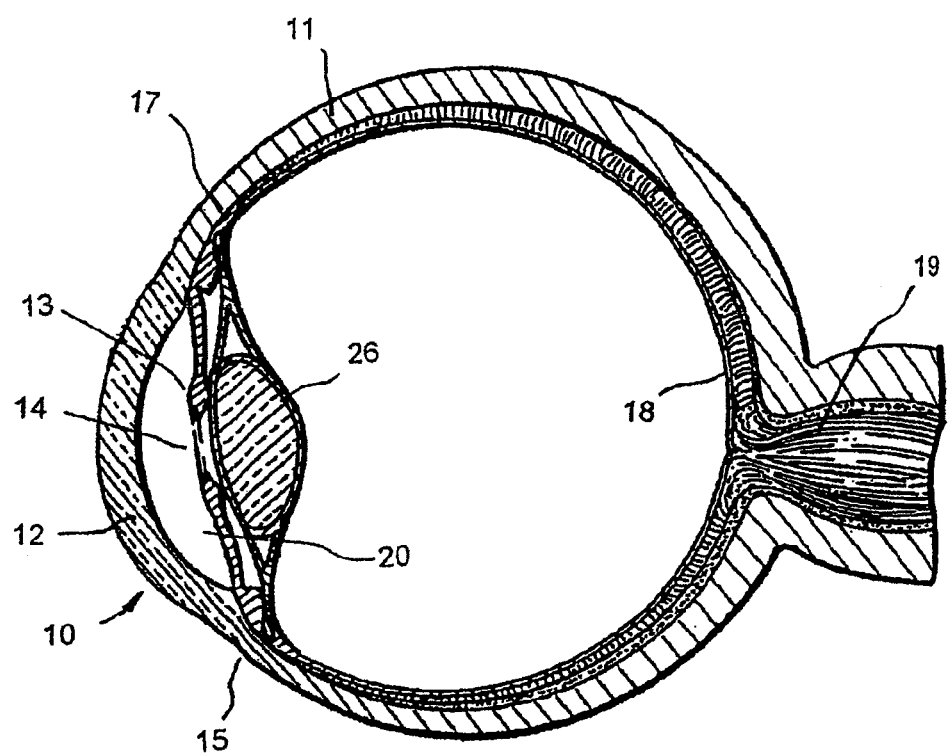
FIG. 1 is a coronal, cross-sectional view of an eye.
Figure 2:
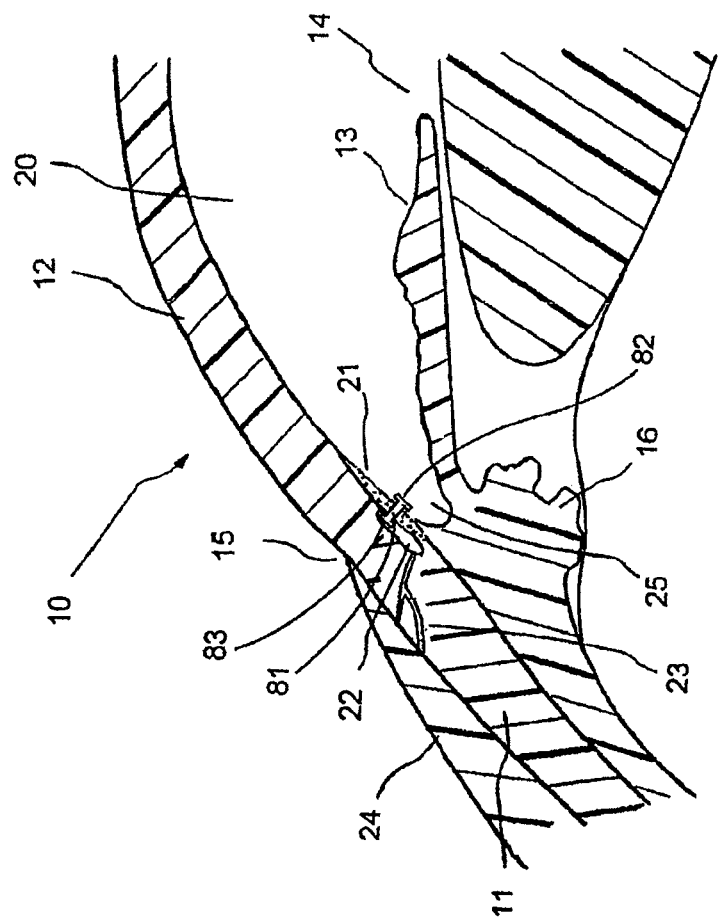
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and a Schlemm's canal 22. A sclera 11 is a thick collagenous tissue that covers the entire eye 10 except a portion that is covered by a cornea 12. The cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

The anterior chamber 20 of the eye 10, which is bound anteriorly by the cornea 12 and posteriorly by the iris 13 and a lens 26, is filled with aqueous humor (hereinafter referred to as "aqueous"). Aqueous is produced primarily by the ciliary body 16, then moves anteriorly through the pupil 14 and reaches an anterior chamber angle 25, formed between the iris 13 and the cornea 12. In a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20, which leads to an increase in intraocular pressure. Fluids are relatively incompressible, and thus intraocular pressure is distributed relatively uniformly throughout the eye 10.

Figure 6:
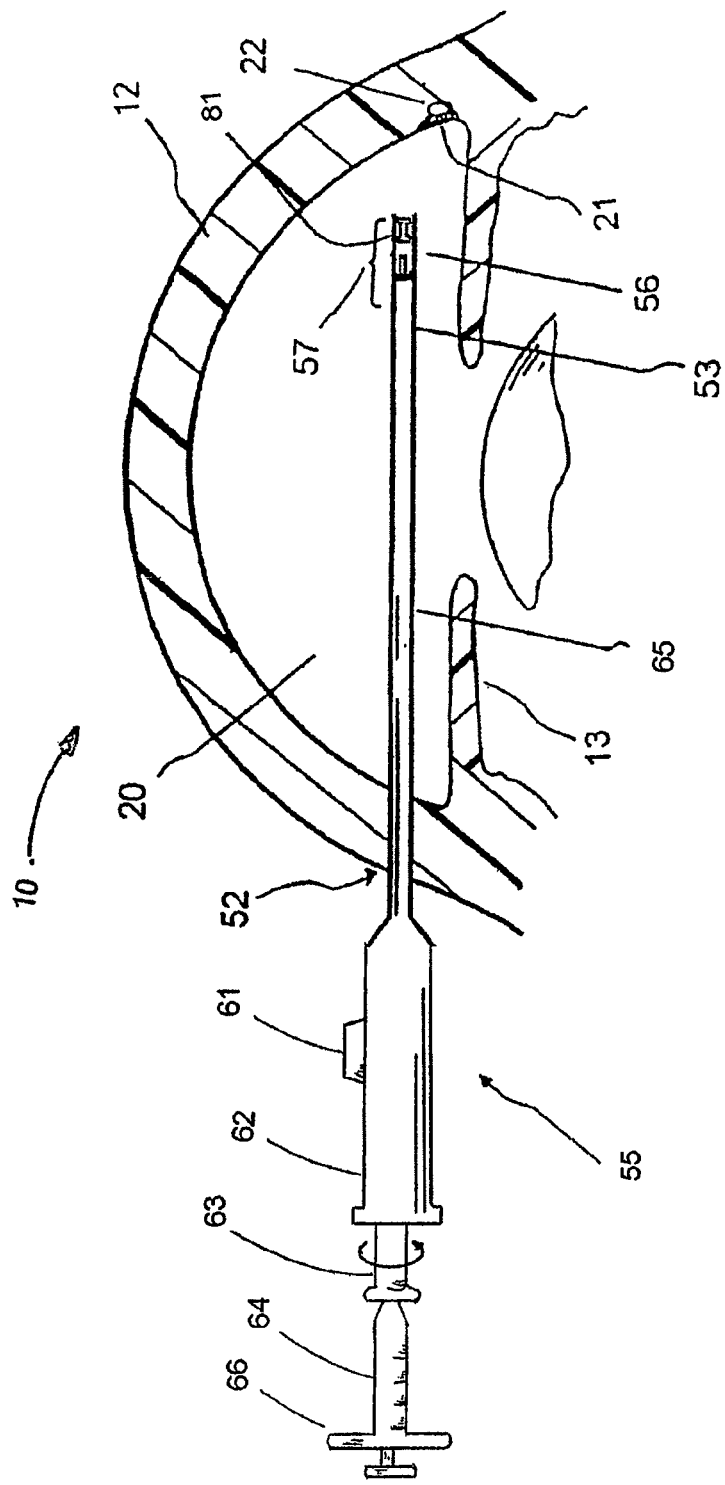
FIG. 6 is an enlarged, cross-sectional view of a preferred method of implanting a trabecular microstent within an eye.

As shown in FIG. 2, the trabecular meshwork 21 is adjacent to a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12. A microstent 81 is shown placed through trabecular meshwork 21 having a distal portion 83 disposed within Schlemm's canal 22 and a proximal portion 82 disposed within the anterior chamber 20 of the eye 10. FIG. 6 generally illustrates the use of one embodiment of a trabecular microstent 81 for establishing an outflow pathway, passing through the trabecular meshwork 21, which is discussed in greater detail below.

Figure 3:
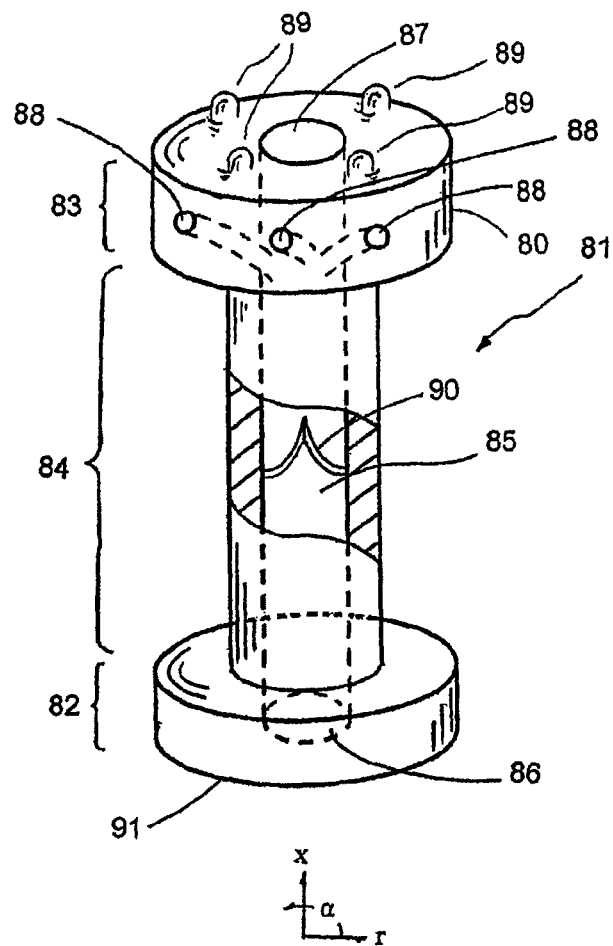
FIG. 3 is an oblique elevation view of one embodiment of an axisymmetric trabecular microstent.

FIG. 3 illustrates a preferred embodiment of a hollow trabecular microstent 81, which facilitates the outflow of aqueous from the anterior chamber 20 into Schlemm's canal 22, and subsequently into the aqueous collectors and the aqueous veins so that intraocular pressure is reduced. In the illustrated embodiment, the trabecular microstent 81 comprises an inlet section 82, having an inlet opening 86, a middle section 84, and an outlet section 83 having at least one opening 87, 88. The middle section 84 may be an extension of, or may be coextensive with, the inlet section 82. The device 81 comprises at least one lumen 85 within section 84, which is in fluid communication with the inlet opening 86 and the outlet opening 87, 88, thereby facilitating transfer of aqueous through the device 81. In one aspect, the outlet side openings 88, each of which is in fluid communication with the lumen 85 for transmission of aqueous, are arranged spaced apart around the circumferential periphery 80 of the outlet section 83. In another aspect, the outlet openings 88 are located and configured to enable jet-like infusing fluid impinging any specific region of Schlemm's canal tissue suitably for tissue stimulation.

As will be apparent to a person skilled in the art, the lumen 85 and the remaining body of the outlet section 83 may have a cross-sectional shape that is oval, circular, or other appropriate shape. Preferably, the middle section 84 has a length that is roughly equal to a thickness of the trabecular meshwork 21, which typically ranges between about 100 μm and about 300 μm.

To further stent or open Schlemm's canal after implanting the axisymmetric device 81, a plurality of elevated (that is, protruding axially) supports or pillars 89 is located at the distal-most end of the outlet section 83 sized and configured for allowing media (for example, aqueous, liquid, balanced salt solution, viscoelastic fluid, therapeutic agents, or the like) to be transported freely.

The microstent 81 may further comprises a flow-restricting member 90, which is tightly retained within a lumen 85. The flow-restricting member 90 serves to selectively restrict at least one component in blood from moving retrograde, i.e., from the outlet section 83 into the anterior chamber 20 of the eye 10. Alternatively, the flow-restricting member 90 may be situated in any location within the device 81 such that blood flow is restricted from retrograde motion. The flow-restricting member 90 is sized and configured for maintaining the pressure of the infused fluid within the aqueous cavity for a suitable period of time. The flow-restricting member 90 may, in other embodiments, be a filter made of a material selected from the following filter materials: expanded polytetrafluoroethylene, cellulose, ceramic, glass, Nylon, plastic, and fluorinated material such as polyvinylidene fluoride ("PVDF") (trade name: Kynar, by DuPont).

The trabecular microstent 81 may be made by molding, thermo-forming, or other micro-machining techniques. The trabecular microstent 81 preferably comprises a biocompatible material such that inflammation arising due to irritation between the outer surface of the device 81 and the surrounding tissue is minimized. Biocompatible materials which may be used for the device 81 preferably include, but are not limited to, titanium, stainless steel, medical grade silicone, e.g., Silastic™, available from Dow Corning Corporation of Midland, Mich.; and polyurethane, e.g., Pellethane™, also available from Dow Corning Corporation. In other embodiments, the device 81 may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In another aspect, the microstent is made of a biodegradable material selected from a group consisting of poly(lactic acid), polyethylene-vinyl acetate, poly(lactic-co-glycolic acid), poly(D,L-lactide), poly(D,L-lactide-co-trimethylene carbonate), poly(caprolactone), poly(glycolic acid), and copolymer thereof.

In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists, TGF-beta, and other anti-glaucoma drugs, or antibiotics), and the like.

As is well known in the art, a device coated or loaded with a slow-release substance can have prolonged effects on local tissue surrounding the device. The slow-release delivery can be designed such that an effective amount of substance is released over a desired duration. "Substance," as used herein, is defined as any therapeutic or active drug that can stop, mitigate, slow-down or reverse undesired disease processes.

In one embodiment, the device 81 may be made of a biodegradable (also including bioerodible) material admixed with a substance for substance slow-release into ocular tissues. In another embodiment, polymer films may function as substance containing release devices whereby the polymer films may be coupled or secured to the device 81. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack.

The device 81 may be used for a direct release of pharmaceutical preparations into ocular tissues. As discussed above, the pharmaceuticals may be compounded within the device 81 or form a coating on the device 81. Any known drug therapy for glaucoma may be utilized.

Figure 4:
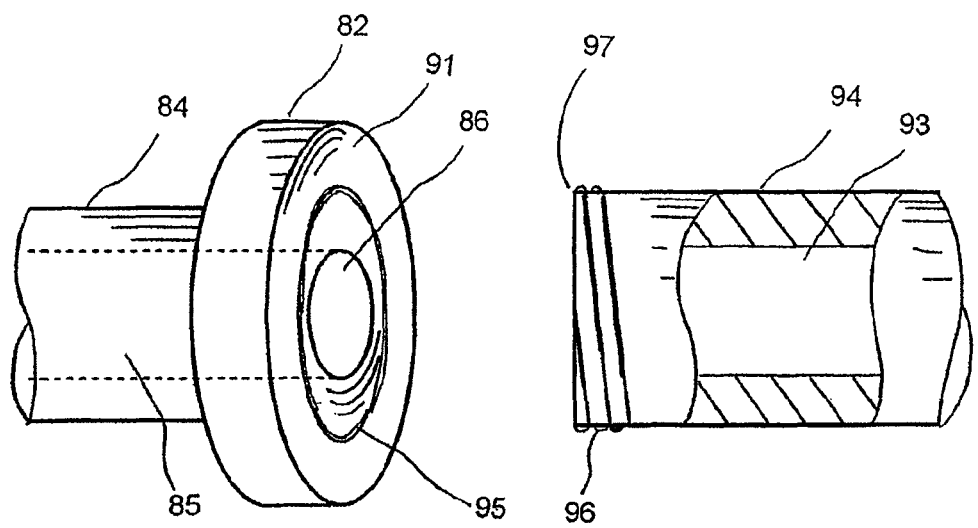
FIG. 4 is a detailed view of the proximal section of the microstent of FIG. 3.

FIG. 4 shows a detailed view of the proximal section 82 of the microstent 81 of FIG. 3. In some aspect, the proximal section 82 has a bottom peripheral surface 91 that is about perpendicular to the lumen 85 of the microstent 81. A receiving thread arrangement 95 is appropriately located on the peripheral surface 91. The receiving thread arrangement 95 is sized and configured to releasably receive a screw thread arrangement 96 for coupling together, wherein the screw thread arrangement 96 is disposed at the distal end 97 of a fluid delivery element 94 which has a lumen 93 for transporting the infusing fluid into the aqueous cavity for therapeutic purposes. The coupling of the receiving thread arrangement 95 and the screw thread arrangement 96 makes the fluid infusion through the lumen 85 leak-proof enabling pressurized the aqueous cavity.

Figure 5:
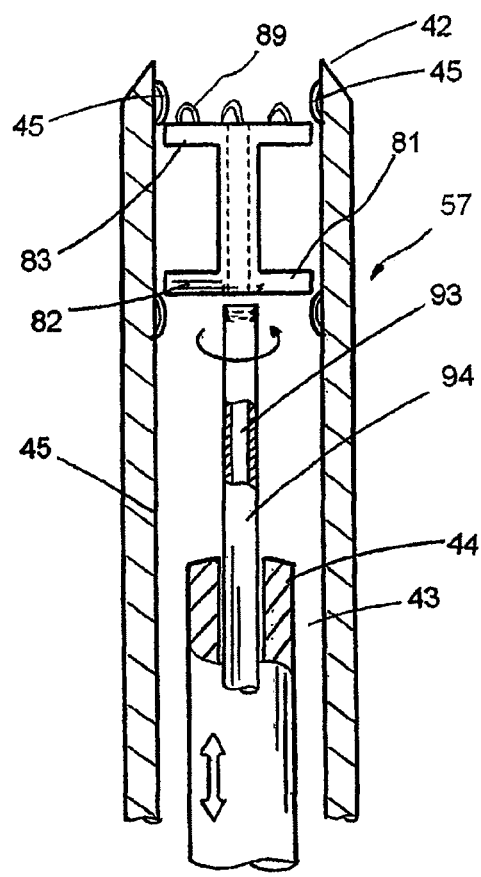
FIG. 5 is an applicator for delivering a microstent and infusing fluid for therapeutic treatment.

FIG. 5 shows a distal portion 57 of an applicator 55 for delivering a microstent 81 and infusing fluid for therapeutic treatment. The distal portion 57 comprises a distal cutting means 42 sharp enough for creating an incision on the cornea and also creating an opening on trabecular meshwork 21 for stent placement. The axisymmetric microstent 81 is snugly placed within the lumen 43 of the applicator 55 and retained by a plurality of stent retaining members 45. The microstent 81 is deployed from the applicator 55 once the distal section 83 passes beyond the edge of the trabecular meshwork 21. In one aspect, the stent deployment is facilitated by a plunger-type deployment mechanism 44 with an associated deployment actuator 61 mounted on the handle 62 of the applicator 55 (see FIG. 6).

The microstent 81 may be releasably coupled with a fluid delivery element 94 at any convenient time during the procedures. In one aspect, the screw-unscrew coupling steps between the microstent 81 and the fluid delivery element 94 is carried out by suitably rotating the fluid delivery element. 94 with reference to the stent receiving thread arrangement 95, wherein the associated rotating mechanism 63 is located at the handle 62 of the applicator 55.

As will be appreciated by those of ordinary skill in the art, the device 81 may advantageously be practiced with a variety of sizes and shapes without departing from the scope of the invention. Depending upon the distance between the anterior chamber 20 and the drainage vessel (e.g., a vein) contemplated, the devices 81 may have a length ranging from about 0.05 centimeters to over 1 centimeter. Preferably, the device 81 has an outside diameter ranging between about 30 μm and about 500 μm, with the lumen 85 having diameters ranging between about 20 μm and about 250 μm, respectively. In addition, the device 81 may have a plurality of lumens to facilitate transmission of multiple flows of aqueous or infusing fluid.

One preferred method for increasing aqueous outflow in the eye 10 of a patient, to reduce intraocular pressure therein, comprises bypassing the trabecular meshwork 21. In operation, the middle section 84 of the device 81 is advantageously placed across the trabecular meshwork 21 through a slit or opening. This opening can be created by use of a laser, a knife, thermal energy (radiofrequency, ultrasound, microwave), cryogenic energy, or other surgical cutting instrument. The opening may advantageously be substantially horizontal, i.e., extending longitudinally in the same direction as the circumference of the limbus 15 (FIG. 2). Other opening directions may also be used, as well. The opening may advantageously be oriented at any angle, relative to the circumference of the limbus 15, that is appropriate for inserting the device 81 through the trabecular meshwork 21 and into Schlemm's canal 22 or other outflow pathway, as will be apparent to those skilled in the art. Furthermore, the outlet section 83 may be positioned into fluid collection channels of the natural outflow pathways. Such natural outflow pathways include Schlemm's canal 22, aqueous collector channels, aqueous veins, and episcleral veins.

FIG. 6 generally illustrates a preferred method by which the trabecular microstent 81 is implanted within the eye 10. In the illustrated method, a delivery applicator 55 is provided, which preferably comprises a syringe portion 64 and a cannula portion 65, which contains at least one lumen 43 in fluid communication with the fluid supply 66. The cannula portion 65 preferably has a size of about 30 gauge. However, in other embodiments, the cannula portion 65 may have a size ranging between about 16 gauges and about 40 gauges. A holder 56 at the distal portion 57 of the cannula portion 65 for holding the device 81 may advantageously comprise a lumen, a sheath, a clamp, tongs, a space, and the like.

In the method illustrated in FIG. 6, the device 81 is placed into the lumen 43 of the delivery applicator 55 and then advanced to a desired implantation site within the eye 10. The delivery applicator 55 holds the device 81 securely during delivery and releases it when the practitioner initiates deployment actuator 61 of the applicator 55.

In a preferred embodiment of trabecular meshwork surgery, a patient is placed in a supine position, prepped, draped, and appropriately anesthetized. A small incision 52 is then made through the cornea 12 with a self-trephining applicator 55. The incision 52 preferably has a surface length less than about 1.0 millimeter in length and may advantageously be self-sealing. Through the incision 52, the trabecular meshwork 21 is accessed, wherein an incision is made with a cutting means 42 enabling forming a hole on the trabecular meshwork 21 for stent placement. The hole on the trabecular meshwork can also be created with a tip having thermal energy or cryogenic energy. After the device 81 is appropriately implanted, the applicator 55 is withdrawn and the trabecular meshwork surgery is concluded.

In some aspect of the present invention, it is provided a method for expanding or attenuating the capacity of the existing canal outflow system (also known as the "aqueous cavity"). This system could have become constricted or blocked due to age or other factors associated with glaucoma. In one aspect, a tight fluid coupling is established between an external pressured fluid source 66 and Schlemm's canal 22 through a microstent 81. It is also advantageous to connect the external pressurized fluid source through a removable instrument (for example, a temporary applicator, catheter, cannula, or tubing) to Schlemm's canal ab interno for applying the fluid infusion therapy.

Once the fluid coupling is established, the pressure in the canal is raised by injecting fluid or fluid with therapeutic substances. In some aspect of the present invention, a method is provided of treating glaucoma including infusing fluid into aqueous cavity from an anterior chamber end of a stent, wherein the fluid is at an elevated pressure above a baseline pressure of the aqueous cavity. The method further comprises placing a hollow trabecular microstent bypassing the trabecular meshwork, wherein the fluid is infused from the anterior chamber through a lumen of the microstent. The mode of fluid injection is selected from a group consisting of a pulsed mode, an intermittent mode, a programmed mode, or combination thereof. In one aspect, the pressure of the fluid therapy is effective to cause therapeutic effects on the tissue of the aqueous cavity. In another aspect, the fluid pressure is effective to cause the dilation of the aqueous cavity beyond the tissue elastic yield point for plastic permanent deformation. In other embodiment, the fluid is at an elevated pressure effective to cause plastic deformation for at least a portion of the aqueous cavity.

The fluid may be a salt solution such as Balanced Salt Solution, a viscoelastic (such as Healon), any other suitable viscous or non-viscous liquid, or suitable liquid loaded with drug at a concentration suitable for therapeutic purposes without causing safety concerns. A combination of liquids may also be used. The pressure is raised at an appropriate rate of rise to an appropriate level and for an appropriate length of time, as determined through development studies, to provide for the expansion of the outflow structures and/or a clearing of any blockages within them. The procedure can be augmented with other aids to enhance its effectiveness. These aids may include heat, vibration (sonic or ultrasonic), pulsation of a pressure front, pH, drugs, etc. It is intended that the aqueous cavity be expanded (attenuation or tissue stimulation) by this procedure resulting in an increased capacity for inflow and outflow of Schlemm's canal.

In some aspect of the present invention, it is provided a method for using a removable applicator, catheter, cannula, or tubing that is placed ab interno through the trabecular meshwork into the aqueous cavity of an eye adapted for infusing therapeutic liquid into the aqueous cavity.

In some aspect of the present invention, it is disclosed a method of treating glaucoma, the method including: providing at least one pharmaceutical substance incorporated into an axisymmetric trabecular microstent; implanting the microstent within a trabecular meshwork of an eye such that a first end of the microstent is positioned in an anterior chamber of the eye while a second end is positioned in a Schlemm's canal, wherein the first and second ends of the microstent establish a fluid communication between the anterior chamber and the Schlemm's canal; and allowing the microstent to release a quantity of the pharmaceutical substance into the eye. In one embodiment, the method further comprises a step of infusing fluid into the Schlemm's canal from the anterior chamber through a lumen of the microstent, wherein the fluid is at an elevated pressure above a baseline pressure of the Schlemm's canal.

Although preferred embodiments of the invention have been described in detail, certain variations and modifications will be apparent to those skilled in the art, including embodiments that do not provide all of the features and benefits described herein. Accordingly, the scope of the present invention is not to be limited by the illustrations or the foregoing descriptions thereof, but rather solely by reference to the appended claims and their equivalents.

What is claimed is:

1. A method of treating glaucoma, comprising:
   inserting an implant through an incision in an eye having an aqueous cavity, the implant having an inflow section that is in fluid communication through an implant lumen with an outflow section of the implant;
   transporting the outflow section through the anterior chamber from the incision to the trabecular meshwork;
   advancing the outflow section through the trabecular meshwork and into the aqueous cavity of the eye;
   positioning the implant such that outflow section is positioned at the aqueous cavity;
   providing a delivery element having a delivery lumen;
   coupling the delivery element to the implant, such that the implant lumen is confluent with the delivery lumen;
   infusing fluid through the delivery lumen to the implant lumen, such that fluid flows from the inflow section to the outflow section, and such that the fluid flows into the aqueous cavity;
   removing the delivery element from the eye while leaving in place the implant; and
   draining aqueous humor through the implant lumen of the implant to the aqueous cavity;
   wherein the aqueous cavity is selected from the group consisting of Schlemm's canal, an aqueous collector channel, and an episcleral vein of the eye.

2. The method of claim 1, wherein said infusing of fluid is at a pressure sufficient to cause plastic deformation of at least a portion of the aqueous cavity.

3. A method of treating glaucoma, comprising:
   inserting an delivery element implant through an incision in an eye, the implant having a lumen and an outflow section that is in fluid communication with the lumen of the implant, wherein the implant remains in the eye after performing the method;
   transporting the outflow section through the anterior chamber from the incision to the trabecular meshwork;
   advancing the outflow section through the trabecular meshwork and into Schlemm's canal of the eye; and applying pressure to a fluid such that the fluid flows through the lumen of the implant and into Schlemm's canal through the outflow section.

4. The method of claim 3, wherein the fluid is other than aqueous humor.

5. The method of claim 3, wherein said fluid is at least one of salt solution or viscoelastic fluid.

6. The method of claim 3, wherein the fluid comprises a therapeutic substance selected from the group consisting of a pharmaceutical, a gene, a growth factor, and an enzyme.

7. The method of claim 3, wherein the fluid comprises a therapeutic substance selected from the group consisting of an antiglaucoma drug, a beta-adrenergic antagonist, a TGF-beta compound, and an antibiotic.

8. The method of claim 3, wherein said pressure is sufficient to cause plastic deformation of at least a portion of Schlemm's canal.

9. The method of claim 8, wherein a temperature of said fluid is raised sufficiently to enhance said plastic deformation.

10. The method of claim 8, wherein a pH of said fluid is adjusted sufficiently to enhance said plastic deformation.

11. The method of claim 3, further comprising vibrating a tissue of said eye.

12. A method of treating glaucoma, comprising:
inserting an implant through an incision in an eye having an aqueous collector channel, the implant having a lumen and an outflow section that is in fluid communication with the lumen of the implant;
transporting the outflow section through the anterior chamber from the incision to the trabecular meshwork;
advancing the outflow section through the trabecular meshwork and into an aqueous collector channel of the eye;
applying pressure to a fluid such that the fluid flows through the lumen of the implant and into the aqueous collector channel through the outflow section; and
draining aqueous humor to the aqueous collector channel through the lumen and the outflow section of the implant.

13. The method of claim 12, wherein the fluid is other than aqueous humor.

14. The method of claim 12, wherein said fluid is at least one of salt solution or viscoelastic fluid.

15. The method of claim 12, wherein the fluid comprises a therapeutic substance selected from the group consisting of a pharmaceutical, a gene, a growth factor, and an enzyme.

16. The method of claim 12, wherein the fluid comprises a therapeutic substance selected from the group consisting of an antiglaucoma drug, a beta-adrenergic antagonist, a TGF-beta compound, and an antibiotic.

17. The method of claim 12, wherein said pressure is sufficient to cause plastic deformation of at least a portion of the aqueous collector channel.

18. The method of claim 17, wherein a temperature of said fluid is raised sufficiently to enhance said plastic deformation.

19. The method of claim 17, wherein a pH of said fluid is adjusted sufficiently to enhance said plastic deformation.

20. The method of claim 12, further comprising vibrating a tissue of said eye.

21. A method of implanting an implant, comprising:
inserting an implant into an anterior chamber of an eye, the implant having a lumen and an outflow section that is in fluid communication with the lumen of the implant;
advancing the implant from within the anterior chamber to an anterior chamber angle;
implanting the implant in ocular tissue of the eye;
coupling a fluid delivery system to the lumen of the implant;
delivering a fluid from the fluid delivery system to the lumen such that the fluid flows through the lumen of the implant and out the outflow section of the implant, wherein the fluid is selected from the group consisting of a sterile saline solution, a salt solution, a balanced salt solution, a viscous fluid, a non-viscous fluid, a viscoelastic, a fluid at an elevated pressure, a fluid at an elevated pressure above a baseline pressure of an aqueous cavity, a fluid at a pH to enhance plastic deformation, a fluid at an elevated temperature, a combination of liquids, and a fluid comprising a therapeutic substance;
decoupling the fluid delivery system from the lumen of the implant;
withdrawing the fluid delivery system from the eye; and
leaving the implant in the eye and draining aqueous humor from the anterior chamber through the lumen of the implant.

22. The method of claim 21 additionally comprising generating with the delivered fluid a pressure effective to cause a dilation of ocular tissue.

23. The method of claim 21 additionally comprising deforming of at least a portion of the ocular tissue with the delivered fluid.

24. The method of claim 23, wherein a temperature of said fluid is raised when deforming at least the portion of the ocular tissue.

25. The method of claim 23, wherein a pH of said fluid is adjusted when deforming at least the portion of the ocular tissue.

26. The method of claim 21, wherein the fluid comprises a therapeutic substance.

27. The method of claim 26, wherein the therapeutic substance is selected from the group comprising a pharmaceutical, a gene, a growth factor, an anti-glaucoma drug, a beta-adrenergic antagonist, a TGF-beta compound, an antibiotic, and an enzyme.

28. The method of claim 21 additionally comprising vibrating the ocular tissue.

* * * * *